United States Patent [19]

Drake

[11] Patent Number: 4,607,131

[45] Date of Patent: Aug. 19, 1986

[54] ISOLATION OF 3-METHYL-1-BUTENE FROM A HYDROCARBON STREAM

[75] Inventor: Charles A. Drake, Bartlesville, Okla.

[73] Assignee: Phillips Petroleum Company, Bartlesville, Okla.

[21] Appl. No.: 696,362

[22] Filed: Jan. 31, 1985

[51] Int. Cl.$^4$ .............................................. C07C 7/17
[52] U.S. Cl. ................................... 585/858; 585/859
[58] Field of Search .............................. 585/858, 859

[56] References Cited

U.S. PATENT DOCUMENTS

| | | | |
|---|---|---|---|
| 2,958,715 | 11/1960 | Sanford et al. | 260/677 |
| 2,968,682 | 1/1961 | Crouse, Jr. et al. | 260/677 |
| 3,185,742 | 5/1965 | Sherk et al. | 260/677 |
| 3,300,539 | 1/1967 | Sherk | 585/858 |
| 3,423,385 | 1/1969 | Bebb et al. | 260/94.2 |
| 3,458,591 | 7/1969 | Bebb et al. | 260/681.5 |
| 3,842,136 | 10/1974 | Wandstrat | 260/677 A |
| 3,864,419 | 2/1975 | Murphy | 260/677 S |
| 4,112,009 | 9/1978 | Rescalli et al. | 260/677 A |

Primary Examiner—William R. Dixon, Jr.
Assistant Examiner—Cynthia A. Prezlock
Attorney, Agent, or Firm—L. M. Lavin

[57] ABSTRACT

A process for recovering 3-methyl-1-butene from a hydrocarbon stream by treating the stream with sulfuric acid to remove compounds which form azeotropes with 3-methyl-1-butene and separating the remaining stream.

8 Claims, No Drawings

ISOLATION OF 3-METHYL-1-BUTENE FROM A HYDROCARBON STREAM

BACKGROUND OF THE INVENTION

This invention relates to the treatment of hydrocarbon containing streams. It also relates to the treatment of amylene streams. In particular it relates to the recovery of 3-methyl-1-butene from a hydrocarbon stream. It further relates to the use of sulfuric acid to treat the amylene stream so that 3-methyl-1-butene can be recovered in a distillation process.

Isolation of 3-methyl-1-butene from certain hydrocarbon streams has become an economically attractive route to obtain 3-methyl-1-butene. However, distillation techniques are not successful for this separation because of an azeotrope formed by 3-methyl-1-butene and other stream components, such as 2-butyne.

The object of this invention is to recover 3-methyl-1-butene from a hydrocarbon stream.

SUMMARY OF THE INVENTION

According to the instant invention a sulfuric acid extraction is utilized to remove compounds which form azeotropes with 3-methyl-1-butene, such as 2-butyne, from a hydrocarbon stream to allow the recovery of 3-methyl-1-butene through conventional separation methods, such as distillation.

DETAILED DESCRIPTION OF THE INVENTION

According to the instant invention any hydrocarbon containing stream which contains 3-methyl-1-butene and compounds which form azeotropes with 3-methyl-1-butene, can be used. Typical streams include the $C_5$- cut of a heavy gas oil catalytic cracking stream. An example of such a stream is a Goodyear amylene stream. This invention is particularly sensitive to the concentration of sulfuric acid used. Generally the sulfuric acid concentration will range from between 70 weight percent to about 85 weight percent. Preferably the sulfuric acid concentration will be about 75 weight percent.

The extraction of the azeotropes using the sulfuric acid can be carried out in any range of temperature from about 5° C. to about 35° C. Preferably the temperature will be around 10° C.

The sulfuric acid can be used in any amount. Generally, it can be used in an amount ranging from about 0.25 to about 20 times the weight of the hydrocarbon stream. Preferably, the amount of sulfuric acid is about five times the weight of the stream to be treated. The acid and the hydrocarbon streams can be contacted from about 0.5 to about 60 minutes. Preferably they are contacted for about 15 minutes, then the insoluble organic phase is separated from the sulfuric acid containing soluble organic compounds.

The extraction process can be carried out in any conventional method for contacting fluids. This invention is not limited by the method employed in contacting the sulfuric acid and the hydrocarbon containing stream. For example, the stream and the sulfuric acid can be contacted in a liquid-liquid extraction process.

3-Methyl-1-butene is recovered from the separated organic layer through conventional separation techniques, such as distillation, extraction, etc. The soluble organic materials dissolved in the sulfuric acid, which also contains acetylenes and dienes, but particularly those compounds that form azeotropes with 3-methyl-1-butene, such as 2-butyne, are further treated to recover the sulfuric acid.

Sulfuric acid is recovered by diluting the acid solvent mixture with sufficient water to cause a separation of the acid from the peviously solubilized hydrocarbons. Once this separation occurs, the sulfuric acid can be removed in any conventional manner and reconstituted to the desired concentration for recycle.

3-Methyl-1-butene is recovered using conventional distillation techniques. The removal of those compounds which form azeotropes allows the recovery of the 3-methyl-1-butene.

The following examples demonstrate the advantages of this invention.

EXAMPLE I

A 220 g sample of "Goodyear amylene stream" was subjected to distillation at atmospheric pressure in a 60 tray Oldershaw distillation column at a reflux ratio of 60/1. Kettle temperature was maintained at 28°-36° C. throughout the distillation, with head temperature of 9°-26° C. for the samples collected. The compositions of several distillation cuts collected are given in Table I.

TABLE I

| Composition of Distillation Fractions from Amylene Streams | | | | | | | | | |
|---|---|---|---|---|---|---|---|---|---|
| | Initial | 1 | 2 | 3 | 4 | 5 | 6 | 7 | Kettle |
| Head Temperature, °C. | — | 9 | 13 | 17 | 20 | 21 | 22 | 24 | — |
| Total % Overhead | — | 1.6 | 3.4 | 7.1 | 11.8 | 16.1 | 20.8 | 24.4 | — |
| Composition, % | | | | | | | | | |
| Butene | 24.1 | 57.4 | 50.2 | 20.1 | 8.1 | 1.9 | 0.4 | 0.1 | — |
| Isopentene | 11.6 | 3.7 | 1.4 | 19.2 | 8.0 | 14.6 | 27.6 | 30.8' | 7.0 |
| *3-MB-1 | 12.3 | 22.4 | 30.9 | 34.2 | 63.7 | 59.5 | 28.3 | 12.4 | 0.5 |
| 1-Pentene | 27.6 | 14.0 | 14.0 | 7.9 | 7.0 | 2.6 | 2.5 | 5.1 | 49.1 |
| 1,4-Pentadiene | 13.7 | 1.5 | 1.4 | 19.8 | 8.1 | 14.8 | 31.3 | 41.1 | 25.1 |
| **2-MB-2 | — | 0.4 | 0.3 | — | — | — | — | — | 8.5 |
| Isoprene | 7.4 | 0.1 | — | 0.2 | 0.1 | 0.1 | 0.1 | 0.1 | 8.5 |
| 2-Butyne | 2.9 | 0.4 | 1.0 | 7.3 | 4.2 | 6.5 | 9.3 | 8.8 | 0.9 |

*3-methyl-1-butene
**2-methyl-2-butene

These distillation results demonstrate that 3-methyl-1-butene cannot be isolated in pure form by simple distillation from a hydrocarbon mixture which includes azeotrope-forming compounds, such as 2-butyne.

EXAMPLE II

Several aliquots of "Goodyear amylene stream" were contacted with sulfuric acid of varied concentrations. The components were cooled to the desired temperature before mixing, then maintained at that temperature with mixing for 10 to 30 minutes before phase separating for organic phase analysis by gas liquid chromatography (glc). The conditions employed, volumes of reagents treated and product analyses are presented in Table II.

TABLE II

Composition of Amylene Stream Samples after Extraction with $H_2SO_4$

| | Initial | Run # 1 | 2 | 3 | 4 | 5 | 6 | 7 | 8 | 9 | 10 | 11 |
|---|---|---|---|---|---|---|---|---|---|---|---|---|
| $H_2SO_4$ Concentration | | | | | | | | | | | | |
| Wt % | — | 65 | 65 | 70 | 75 | 75 | 75 | 75 | 75 | 75 | 80 | 85 |
| Wt acid, g | — | 300 | 300 | 300 | 300 | 300 | 300 | 120 | 120 | 120 | 300 | 300 |
| Wt amylene stream, g | — | 60 | 60 | 60 | 60 | 60 | 60 | 60 | 60 | 60 | 60 | 60 |
| Wt organics recovered, g | — | — | — | 50 | 46 | 50 | 48 | — | — | — | 42 | 40 |
| Contact | | | | | | | | | | | | |
| Time, min. | — | 15 | 30 | 15 | 15 | 15 | 30 | 10 | 20 | 30 | 15 | 15 |
| Temperature, °C. | — | 25 | 25/35 | 10 | 10 | 15 | 15/25 | 25 | 25 | 25 | 10 | 10 |
| Composition. % by glc | | | | | | | | | | | | |
| Butane | 0.1 | 0.2 | 0.4 | 0.2 | 0.3 | 0.2 | 0.3 | 0.2 | 0.3 | 0.3 | 0.5 | 0.4 |
| Butenes | 24.1 | 7.3 | 5.7 | 10.5 | 4.2 | 5.4 | 3.8 | 7.5 | 5.5 | 4.8 | 2.0 | 0.5 |
| Isopentane | 11.6 | 14.9 | 15.9 | 13.6 | 19.8 | 16.7 | 18.9 | 15.3 | 17.6 | 19.0 | 26.5 | 70.4 |
| 3-MB-1 | 12.3 | 14.1 | 14.4 | 12.2 | 15.8 | 14.6 | 14.1 | 14.4 | 15.2 | 14.8 | 15.0 | 3.8 |
| 1-Pentene | 27.6 | 34.0 | 35.7 | 39.4 | 38.1 | 39.1 | 43.2 | 33.2 | 37.1 | 40.4 | 36.5 | 6.8 |
| 1,4-Pentadiene | 13.7 | 16.2 | 16.7 | 14.2 | 18.9 | 16.7 | 17.0 | 17.0 | 17.9 | 17.8 | 18.0 | 8.1 |
| 2-MB-2 | — | 6.9 | 6.5 | 2.5 | 1.5 | 3.1 | 1.5 | 6.0 | 3.0 | 1.7 | 0.4 | 5.2 |
| Isoprene | 7.4 | 3.3 | 2.2 | 4.7 | — | 2.1 | — | 3.7 | 1.2 | 0.1 | — | — |
| 2-Butyne | 2.9 | 1.9 | 1.6 | 2.1 | — | 1.2 | 0.1 | 1.9 | 1.2 | 0.1 | — | — |

The data in Table II demonstrate that essentially all of the 2-butyne can be removed from Goodyear amylene stream by contacting with sulfuric acid under the appropriate treating conditions. Isoprene can also be removed through this method. Essentially complete removal of 2-butyne can be obtained with sulfuric acid concentration greater than or equal to 75%. Weight ratios of acid to amylene stream of 2:1 are operable (See run 9), but ratios are greater than 2:1 are preferred (see run 4). Runs 4 and 10 represent the most effective removal of 2-butyne, with run 4 giving optimal 3-MB-1 recovery (minimal 3-MB-1 loss). The 3-MB-1 can now be obtained from the stream through usual concentration and separation techniques.

EXAMPLE III

Hydrotreating of an amylene stream also serves to remove azeotrope-forming compounds such as 2-butyne and dienes. About 260 g of Goodyear amylene stream which had been hydrotreated to remove these compounds was subjected to distillation at atmospheric pressure in a 60 tray Oldershaw column at a reflux ratio of 60/1. Kettle temperature was maintained at 28°-33° C. throughout the distillation, with head temperature varying, from 11°-26° C. for the samples collected. The compositions of the distillation cuts collected are given in Table III.

TABLE III

Composition of Distillation Fractions of Hydrotreated Amylene Stream

| | Sample # 1 | 2 | 3 | 4 | 5 | 6 | 7 | Kettle |
|---|---|---|---|---|---|---|---|---|
| Head Temperature, °C. | 11 | 15 | 17 | 20 | 23 | 25 | 26 | — |
| Total % Overhead | 3.0 | 5.5 | 9.6 | 13.0 | 18.3 | 21.5 | 25.1 | — |
| Composition, % | | | | | | | | |
| Butenes | 58.3 | 42.1 | 11.1 | 3.5 | 1.6 | 2.8 | 4.9 | 27.0 |
| Isopentane | 3.6 | 2.5 | 3.6 | 8.0 | 22.5 | 50.8 | 55.6 | 8.2 |
| 3-MB-1 | 24.6 | 52.1 | 81.3 | 80.3 | 58.0 | 20.2 | 8.5 | 0.3 |
| 1-Pentene | 1.1 | 0.3 | 0.3 | 0.8 | 4.3 | 11.1 | 20.3 | 44.4 |
| 1,4-Pentadiene | 20.0 | 1.8 | 3.2 | 7.1 | 13.3 | 14.7 | 10.4 | 3.2 |

This experiment demonstrates the improved concentration of 3-methylene-1-butene (3-MB-1) possible by distillation of an amylene stream from which azeotrope forming compounds have been removed.

I claim:

1. A process for recovering 3-methyl-1-butene from a hydrocarbon stream containing 3-methyl-1-butene and 2-butyne which forms an azeotrope with 3-methyl-1-butene said process comprising contacting said stream with sulfuric acid having a concentration ranging from 70 to 85 weight percent to form a soluble fraction containing said 2-butyne and said sulfuric acid and an insoluble fraction which contains said 3-methyl-1-butene and recovering said 3-methyl-1-butene through conventional separation techniques.

2. A process according to claim 1 where said sulfuric acid is used in an amount ranging from about 0.25 to about 20 times the weight of said hydrocarbon stream.

3. A process according to claim 1 where said hydrocarbon containing stream contains amylenes.

4. A process according to claim 3 where said hydrocarbon containing stream is a $C_5$-cut from a heavy gas oil catalytic cracking stream.

5. A process according to claim 1 where said contacting takes place at a temperature ranging from about 5° C. to about 35° C. for about 0.5 to about 60 minutes.

6. A process according to claim 1 where a sulfuric acid layer is recovered, treated with excess water, separated from previously soluble hydrocarbons, and reconstituted for reuse.

7. A process according to claim 3 where said sulfuric acid is used in an amount greater than 2 times the amount of amylenes present in the hydrocarbon stream.

8. A process according to claim 1 wherein said 3-methyl-1-butene is recovered by distillation.

* * * * *